United States Patent [19]

Boo et al.

[11] Patent Number: 5,602,259
[45] Date of Patent: Feb. 11, 1997

[54] METHOD FOR PRODUCING 4-HYDROXY-5-METHYL-3[2H]-FURANONE AND USES OF SAME

[75] Inventors: Yong C. Boo, Suwon; Che O. Jeon, Seoul; Byeong G. Lee; Kyung W. Ro, both of Suwon; Eun J. Kim, Seoul, all of Rep. of Korea

[73] Assignee: Pacific Corporation, Rep. of Korea

[21] Appl. No.: 355,328

[22] Filed: Dec. 12, 1994

[30] Foreign Application Priority Data

Dec. 17, 1993 [KR] Rep. of Korea ............... 1993-28308
Apr. 21, 1994 [KR] Rep. of Korea ............... 1994-08411

[51] Int. Cl.$^6$ ........................................... C07D 307/32
[52] U.S. Cl. ........................................... 549/313; 424/195.1
[58] Field of Search .................... 424/195.1; 549/477, 549/313

[56] References Cited

FOREIGN PATENT DOCUMENTS 0398417  11/1990  European Pat. Off. .
 532120   3/1993  European Pat. Off. .

OTHER PUBLICATIONS

1988 Oerganin Journals Ltd., The Antioxidants of Higher Plants, Richard A. Larson, pp. 960–978.

*Primary Examiner*—Amelia Owens
*Attorney, Agent, or Firm*—Nixon & Vanderhye

[57] ABSTRACT

Disclosed herein is a method for producing 4-hydroxy-5-methyl-3[2H]-furanone and new uses thereof.

4-hydroxy-5-methyl-3[2H]-furanone may be extracted from the plants of *Pinaceae* species and may advantageously be used as an anti-oxidant or for whitening the skin. The compound or extracts containing same is not irritative to the skin and can safely be applied to the skin.

3 Claims, 5 Drawing Sheets

METHOD FOR PRODUCING 4-HYDROXY-5-METHYL-3[2H]-FURANONE AND USES OF SAME

BACKGROUND OF THE INVENTION

1. Field of the Invention

The present invention is related to new uses of 4-hydroxy-5-methyl-3[2H]-furanone and a method for producing the same, and particularly it is related to an anti-oxidative composition and a skin-whitening composition which comprise as an active ingredient 4-hydroxy-5-methyl-3[2H]-furanone, and to a method for producing the same from the plant of *Pinaceae* species.

2. Description of Prior Art

Conventional synthetic anti-oxidants have a drawback that they contain toxic materials which may be incorporated during the synthesis process. To avoid this problem, a naturally occurring anti-oxidant as an alternative of synthetic anti-oxidant are proposed(Phytochemistry, 27(4): 969–978(1988)). Thereafter, many naturally occurring anti-oxidants are developed and examples of typical natural anti-oxidants may include L-ascorbic acid, kojic acid, their derivatives and the like.

The present inventors also made extensive researches to develop a naturally occurring anti-oxidant which shows an excellent anti-oxidation activity as well as can be safely employed. Particularly, the inventors screened various plants for their anti-oxidation action, and as a result thereof, found that the plants of *Pinaceae* species showed a stronger anti-oxidation action than other plants. We made further studies to find out the active components having anti-oxidation action from the plants of *Pinaceae* species and, for the first time, isolated and identified the active component, 4-hydroxy-5-methyl-3[2H]-furanone.

Although there has been suggested that the plants of *Pinaceae* species show an anti-oxidation activity, the active compound has not yet isolated nor identified.

Moreover, we surprisingly found that 4-hydroxy-5-methyl-3[2H]-furanone also has an ability to inhibit melanin formation.

SUMMARY OF THE INVENTION

Thus, an object of the present invention is to provide new uses of 4-hydroxy-5-methyl-3[2H]-furanone.

Another object of the invention is to provide an anti-oxidative composition which comprises as an active ingredient an effective amount of 4-hydroxy-5-methyl-3[2H]-furanone.

Still another object of the invention is to provide a composition for whitening the skin which comprises as an active ingredient an effective amount of 4-hydroxy-5-methyl-3[2H]-furanone.

Further, another object of the present invention is to provide a method for producing 4-hydroxy-5-methyl-3[2H]-furanone, which comprises the steps of:
(a) extracting 4-hydroxy-5-methyl-3[2H]-furanone from the barks or needles of the plants of *Pinaceae* species with a polar solvent;
(b) evaporating an extract obtained in the step (a) to give a concentrate and distributing the concentrate with water and an oil-soluble solvent to give an aqueous layer;
(c) evaporating the aqueous layer of the step (b), and subjecting the resulting concentrate to a chromatography on a reverse phase distribution column employing as an eluant a mixture of water:acetonitrile:methanol= 70–95:0–20:2.5–30% by weight to give active fractions containing 4-hydroxy-5-methyl-3[2H]-furanone; and
(d) recrystallizing the active fractions with water or methanol to give a purified 4-hydroxy-5-methyl-3[2H]-furanone. The other features and applications of the present invention will be easily apparent to those who skilled in the art by the following detailed description.

DETAILED DESCRIPTION OF THE INVENTION 4-hydroxy-5-methyl-3[2H]-furanone is represented by the following formula:

and has been commonly used as a flavoring agent for foods. There has been no attempt to use 4-hydroxy-5-methyl-3[2H]-furanone as an anti-oxidant or the like. Thus, the present inventors for the first time found out that 4-hydroxy-5-methyl-3[2H]-furanone has a strong anti-oxidation action and a skin-whitening activity.

As substances commonly used for whitening the skin, there may be examplified ascorbic acid or kojic acid, or derivatives thereof. However, ascorbic acid or its derivatives are unstable in an aqueous medium and liable to oxidations, and cause irritations to the skin. Kojic acid also has drawbacks that its skin-whitening activity is insufficient and it is unstable.

Although there have been proposed some extracts of plants or herbs as an effective skin-whitening substance, they have a drawback that their deep color deteriorates the appearances of final product. Further, since the active ingredient has not been isolated nor identified, a constant skin-whitening action can not be expected.

4-hydroxy-5-methyl-3[2H]-furanone of the present invention avoid the above-described prior art problems. Thus, 4-hydroxy-5-methyl-3[2H]-furanone has a strong anti-oxidation activity and an excellent action to inhibit melanin formation, and is stable for a long period of time. Moreover, it causes no irritation to the skin.

The anti-oxidation activity of 4-hydroxy-5-methyl-3[2H]-furanone is superior over maltol, kojic acid or L-ascorbic acid, which are commonly used as an anti-oxidant. This is likely due to the structural difference between maltol or kojic acid and 4-hydroxy-5-methyl-3[2H]-furanone: maltol and kojic acid have a six-membered ring while 4-hydroxy-5-methyl-3[2H]-furanone has a five-membered ring. Further, 4-hydroxy-5-methyl-3[2H]-furanone shows a superior action over L-ascorbic acid which also has a five-membered ring, indicating that 4-hydroxy-5-methyl-3[2H]-furanone has the most appropriate structure for anti-oxidant action.

According to the present invention, 4-hydroxy-5-methyl-3[2H]-furanone may be advantageously incorporated as an anti-oxidant into medicines, cosmetics or foods. The amount of 4-hydroxy-5-methyl-3[2H]-furanone is not particularly limited and may be selected within the range showing the anti-oxidation activity without any difficulty by those who skilled in the art.

Further, 4-hydroxy-5-methyl-3[2H]-furanone may be incorporated into cosmetic compositions for the purposes of retarding the aging of the skin, or of whitening the skin. The amount of 4-hydroxy-5-methyl-3[2H]-furanone is not particularly limited. However, it may preferably be in the range of 0.1 to 3% by weight based on the total weight of the composition. A crude extract containing 4-hydroxy-5-methyl-3[2H]-furanone also can be incorporated into cosmetic compositions. For this case, the amount of the extract to be incorporated is decided such that the content of 4-hydroxy-5-methyl-3[2H]-furanone is in the range of 0.1 to 3% by weight based on the tatal weight of the composition. If the content of 4-hydroxy-5-methyl-3[2H]-furanone is less than the lower limit, the effects are not satisfactory, and the content is more than the upper limit, there may be caused an irritation to the skin.

Cosmetic compositions containing 4-hydroxy-5-methyl-3[2H]-furanone may be in the forms of, not intended to be limited thereto, skin care and make-up cosmetic compositions. The form of cosmetic compositions may be easily selected by those skilled in the art and does not limit the scope of the invention.

4-hydroxy-5-methyl-3[2H]-furanone may be produced by extracting the plants or herbs. Particularly, the plants of *Pinaceae* species are advantageously employed for the extraction of 4-hydroxy-5-methyl-3[2H]-furanone. An example of the plant of *Pinaceae* species may include, not limited thereto, *Pinus densiflora* Siebold et Zuccarini, *Pinus rigida* Mill and the like. Any parts of the plants of *Pinaceae* species can be used for extraction, and barks, needles or roots may be advantageously employed. Although, there have been reported some synthetic procedures for producing 4-hydroxy-5-methyl-3[2H]-furanone(EP 0,532,120 A1 and EP 0,398,417 A1), these methods have a drawback that a toxic material can be incorporated into the final reaction product.

The method of extracting 4-hydroxy-5-methyl-3[2H]-furanone from the plant of *Pinaceae* species is not particularly limited. Nevertheless, the present inventors had studied to develop a method for extracting 4-hydroxy-5-methyl-3[2H]-furanone with a high yield and purity.

The method of producing 4-hydroxy-5-methyl-3[2H]-furanone according to the present invention is described below.

The barks, roots or needles of the plant of *Pinaceae* species are immersed in a polar solvent such as water, methanol, ethanol, propanol, or acetone, in single or mixtures thereof to effect an extraction. The extraction may be carried out at room temperature for several days or under heating for several hours.

Then the extract obtained is evaporated to give a concentrate, to which water and an oil-soluble solvent were added, and a distribution is carried out to give an aqueous layer. This distribution procedure may be carried out once or two or more times. As an oil-soluble solvent, there may be employed, but not limited thereto, benzene, cyclohexane, toluene, n-hexane and the like. In the case that the distribution was repeated two or more times, the oil-soluble solvent for each distribution may be the same or different to each other.

The aqueous layer was evaporated and the resulting concentrate is subjected to a chromatography on a reverse phase distribution column employing as an eluant a mixture of water:acetonitrile:methanol=70–95:0–20:2.5–30% by weight to give active fractions showing an anti-oxidation activity. As a reverse phase distribution column, Lichrosorb RP-18 column packed with octadecylated silica may be preferably employed.

The active fractions containing 4-hydroxy-5-methyl-3[2H]-furanone were recrystallized with water or methanol to give a purified 4-hydroxy-5-methyl-3[2H]-furanone as a colorless crystal.

The method according to the present invention has an advantage that it can provide a purified 4-hydroxy-5-methyl-3[2H]-furanone which is free of any toxic substances.

Further, the present method has another advantage that it produces a highly purified 4-hydroxy-5-methyl-3[2H]-furanone without a loss, while the conventional purification methods comprise a distillation step wherein the high temperature employed in the distillation destructs 4-hydroxy-5-methyl-3[2H]-furanone and reduce the yield.

The reverse phase distribution column employed in the present method also can be used for purifying 4-hydroxy-5-methyl-3[2H]-furanone which is produced by any synthetic process.

Moreover, since the plants of *Pinaceae* species are abundant, it is possible to produce 4-hydroxy-5-methyl-3[2H]-furanone in a large amount.

4-hydroxy-5-methyl-3[2H]-furanone obtained by the method of the invention has an excellent activity to inhibit melanin formation. When a fibroblast cell is cultivated for 48 hours in a culture medium incorporated with 4-hydroxy-5-methyl-3[2H]-furanone, L-ascorbic acid or kojic acid, ascorbic acid shows a cytotoxicity at a concentration of 50 ppm while 4-hydroxy-5-methyl-3[2H]-furanone nor kojic acid exhibit no cytotoxicity up to 500 ppm. Further, 4-hydroxy-5-methyl-3[2H]-furanone at 10 or 20 ppm exhibits a significant inhibitive effect on melanin formation within melanoma cells while kojic acid shows an effect at about 400 ppm. Accordingly, 4-hydroxy-5-methyl-3[2H]-furanone has been affirmed to be more safe in the living body than L-ascorbic acid as well as to be more effective in inhibiting melanin formation than kojic acid.

PREFERRED EMBODIMENTS OF THE INVENTION

The present invention shall be described in more detail by the following non-limiting Examples.

EXAMPLE 1

To the dried barks (50 g) of pine tree(*Pinus densiflora* Siebold et Zuccarini) was added 1000 ml of aqueous 50% ethanol solution, and the mixture was heated to about 70° C.

for 4 hours and filtered. The filtrate was evaporated to give a concentrated extract. Each 500 ml of water and toluene was added to the concentrated extract(roughly 12 g) and a distribution was carried out to give an aqueous layer.

A material(roughly 8 g) obtained by evaporating the aqueous layer was subjected to a chromatography on Lichrosorb RP-18 column(3.5×35 cm, Merck) employing as an eluant a mixture of water:acetonitrile:methanol= 80:10:10% by weight to give active fractions containing 4-hydroxy-5-methyl-3[2H]-furanone. The active fractions are combined together, evaporated and recrystallized with methanol to give about 0.2 g(yield 0.4%) of 4-hydroxy-5-methyl-3[2H]-furanone.

EXAMPLE 2

The dried needles (50 g) of pine tree(*Pinus densiflora* Siebold et Zuccarini) was immersed in 1000 ml of aqueous 50% acetone solution at room temperature for 7 days and the resulting solution was filtered. The filtrate was evaporated to give a concentrated extract. Each 500 ml of water and cyclohexane was added to the concentrated extract(roughly 14 g) and a distribution was carried out to give an aqueous layer.

A material(roughly 10 g) obtained by evaporating the aqueous layer was subjected to a chromatography on Lichrosorb RP-18 column(3.5×35 cm, Merck) employing as an eluant a mixture of water:acetonitrile:methanol= 95:2.5:2.5% by weight to give active fractions containing 4-hydroxy-5-methyl-3[2H]-furanone. The active fractions are combined together, evaporated and recrystallized with water to give about 0.2 g(yield 0.4%) of 4-hydroxy-5-methyl-3[2H]-furanone.

EXAMPLE 3

The dried barks (50 g) of pine tree(*Pinus rigida* Mill) was immersed in 1000 ml of aqueous 90% methanol solution at about 70° C. for 4 hours and the resulting solution was filtered. The filtrate was evaporated to give a concentrated extract. Each 500 ml of water and benzene was added to the concentrated extract(roughly 15 g) and a distribution was carried out to give an aqueous layer.

A material(roughly 10 g) obtained by evaporating the aqueous layer was subjected to a chromatography on Lichrosorb RP-18 column(3.5×35 cm, Merck) employing as an eluant a mixture of water:acetonitrile:methanol= 70:20:10% by weight to give active fractions containing 4-hydroxy-5-methyl-3[2H]-furanone. The active fractions are combined together, evaporated and recrystallized with water to give about 0.3 g(yield 0.6%) of 4-hydroxy-5-methyl-3[2H]-furanone.

EXAMPLE 4

The dried needles (50 g) of pine tree(*Pinus rigida* Mill) was immersed in 1000 ml of aqueous 30% propanol solution at room temperature for 10 days and the resulting solution was filtered. The filtrate was evaporated to give a concentrated extract. Each 500 ml of water and n-hexane was added to the concentrated extract(roughly 13 g) and a distribution was carried out to give an aqueous layer.

A material(roughly 11 g) obtained by evaporating the aqueous layer was subjected to a chromatography on Lichrosorb RP-18 column(3.5×35 cm, Merck) employing as an eluant a mixture of water:methanol=70:30% by weight to give active fractions containing 4-hydroxy-5-methyl-3[2H]-furanone. The active fractions are combined together, evaporated and recrystallized with water to give about 0.3 g(yield 0.6%) of 4-hydroxy-5-methyl-3[2H]-furanone.

EXAMPLE 5

The dried needles (500 g) of pine tree(*Pinus densiflora* Siebold et Zuccarini) was immersed in 10 l of aqueous 50% ethanol solution at about 70° C. for 4 hours and the resulting solution was filtered. The filtrate was evaporated under vacuum to give a concentrated extract(120 g). Thus obtained extract contained about 0.5% by weight of 4-hydroxy-5-methyl-3[2H]-furanone. Each 500 ml of water and n-hexane was added to the concentrated extract and a distribution was carried out to give an aqueous layer. The aqueous layer was subjected to distributions three times using 500 ml of n-butanol.

The n-butanol extract was evaporated under vacuum to give a partially purified extract(24 g) containing about 9% by weight of 4-hydroxy-5-methyl-3[2H]-furanone. The partially purified extract was subjected to a chromatography on Lichrosorb RP-18 column(8×50 cm, Merck) employing as an eluant a mixture of water:acetonitrile:methanol= 80:10:10% by weight to give active fractions containing 4-hydroxy-5-methyl-3[2H]-furanone. The active fractions are combined together, evaporated and recrystallized with methanol to give about 2 g(yield 0.4%) of 4-hydroxy-5-methyl-3[2H]-furanone.

The active fractions obtained in Examples 1 through 5 were identified and examined for their physicochemical properties. As a result thereof, the active ingredient is identified as 4-hydroxy-5-methyl-3[2H]-furanone as described below.

EXPERIMENTAL EXAMPLE 1

Structural Analysis

Each of 4-hydroxy-5-methyl-3[2H]-furanone obtained in Examples 1 through 5 was examined for its melting point, elemental analysis, UV, IR, NMR, and MS spectrum.

The apparatuses for carrying out each analysis were are as follows:

Melting Point(mp): Thomas Hoover capillary melting point apparatus) was employed.

Elemental analysis: Carlo-erba elemental analyzer model 1106 was employed.

UV spectrum: Cecil CE5500 spectrometer was employed.

IR spectrum: BioRad FTS-40 spectrometer was employed:

$^1$H and $^{13}$C-NMR spectrum: Bruker AM 500 spectrometer was employed:

MS spectrum: Jeol JMS-DX 303 spectrometer was employed.

The results were listed below and particularly the spectral results were shown in the accompanying FIG. 1 through 4.

m.p. 120°~121° C.;

Elemental analysis for $C_5H_6O_3$: Calculated: C(52.62%), H(5.30%), O(42.08%) Experimental: C(52.48%), H(5.50%)

UV $\lambda_{max}$ (MeOH) 290 nm($\epsilon$=9150)

IR $v_{max}$ cm$^{-1}$(KBr) 3190, 2953, 1698, 1639, 1461, 1315, 1195, 1145, 999, 920, 704

$^1$H NMR(DMSO-d$_6$) $\delta$, ppm from TMS, 2.11(3H, s), 4.51(2H, s), 8.31(1H, s)

$^{13}$C NMR(DMSO-d$_6$) $\delta$ 13.12, 72.58, 134.56, 173.03, 195.48

MS, m/z(%), 114(85.8), 85(1.9), 71(4.8), 55(16.0), 43(100)

EXPERIMENTAL EXAMPLE 2

Anti-oxidation Activity of
4-hydroxy-5-methyl-3[2H]-furanone (1)

An anti-oxidation activity of 4-hydroxy-5-methyl-3[2H]-furanone was examined as follows:

To 1.0 ml of 0.2M potassium phosphate buffer(pH 7.4) containing 2 mg/ml of linolenic acid and 10 mg/ml of Tween-20 was added the extract obtained from Lichrosorb RP-18 column in Example 1, which contains a serial concentrations of 10~2000 ppm of 4-hydroxy-5-methyl-3[2H]-furanone. As controls, a solution of maltol or kojic acid having a serial concentration from 10 to 2000 ppm was added. The resulting mixture was allowed at 37° C. for 24 hours. 0.1 ml of the reaction mixture was taken and diluted with 9.7 ml of ethanol. 0.1 ml of 30% ammonium thiocyanide and 0.1 ml of a mixture of 5% ferrous ammonium sulfate and 3.5% chloric acid were added, and 3 minutes later, an absorbance at 500 nm was measured to evaluate an automatic oxidation of fatty acid.

As a result thereof, the extract showed 90% inhibition of autonomous oxidation of an unsaturated fatty acid, linolenic acid at a concentration of 32 ppm of 4-hydroxy-5-methyl-3[2H]-furanone while maltol or kojic acid showed at a concentration of 460 ppm or 600 ppm, respectively. Accordingly, the extract of the present invention, which contains 4-hydroxy-5-methyl-3[2H]-furanone exhibited an anti-oxidation activity which is 14 folds or 19 folds higher than maltol or kojic acid, respectively.

EXPERIMENTAL EXAMPLE 3

Anti-oxidation Activity of
4-hydroxy-5-methyl-3[2H]-furanone (2)

An anti-oxidation activity of 4-hydroxy-5-methyl-3[2H]-furanone was examined as follows:

1.0 ml of 0.2M potassium phosphate buffer(pH 7.4) containing 2mg/ml of linolenic acid, 10 mg/ml of Tween-20 and 200 ppm of L-ascorbic acid, tocopherol or 4-hydroxy-5-methyl-3[2H]-furanone was allowed to stand at 37° C. for 24 hours. For a control, 1.0 ml of 0.2M potassium phosphate buffer(pH 7.4) containing 2 mg/ml of linolenic acid and 10 mg/ml of Tween-20 was employed.

The same procedure as that of Experimental Example 2 was carried out to evaluate the anti-oxidation activity of test compounds.

Figure 1:
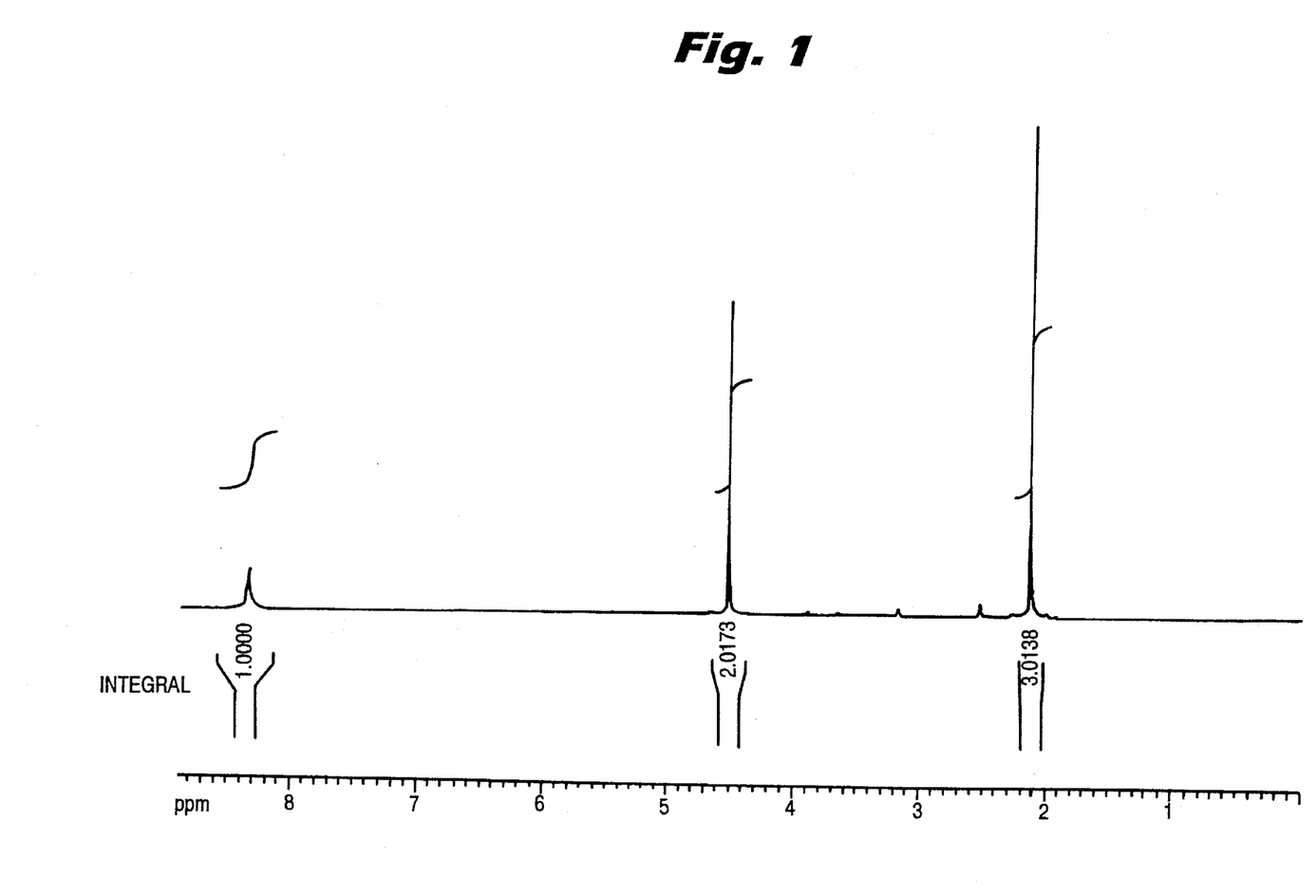
FIG. 1 is a $^1$H-NMR spectrum of 4-hydroxy-5-methyl-3[2H]-furanone.
Figure 2:
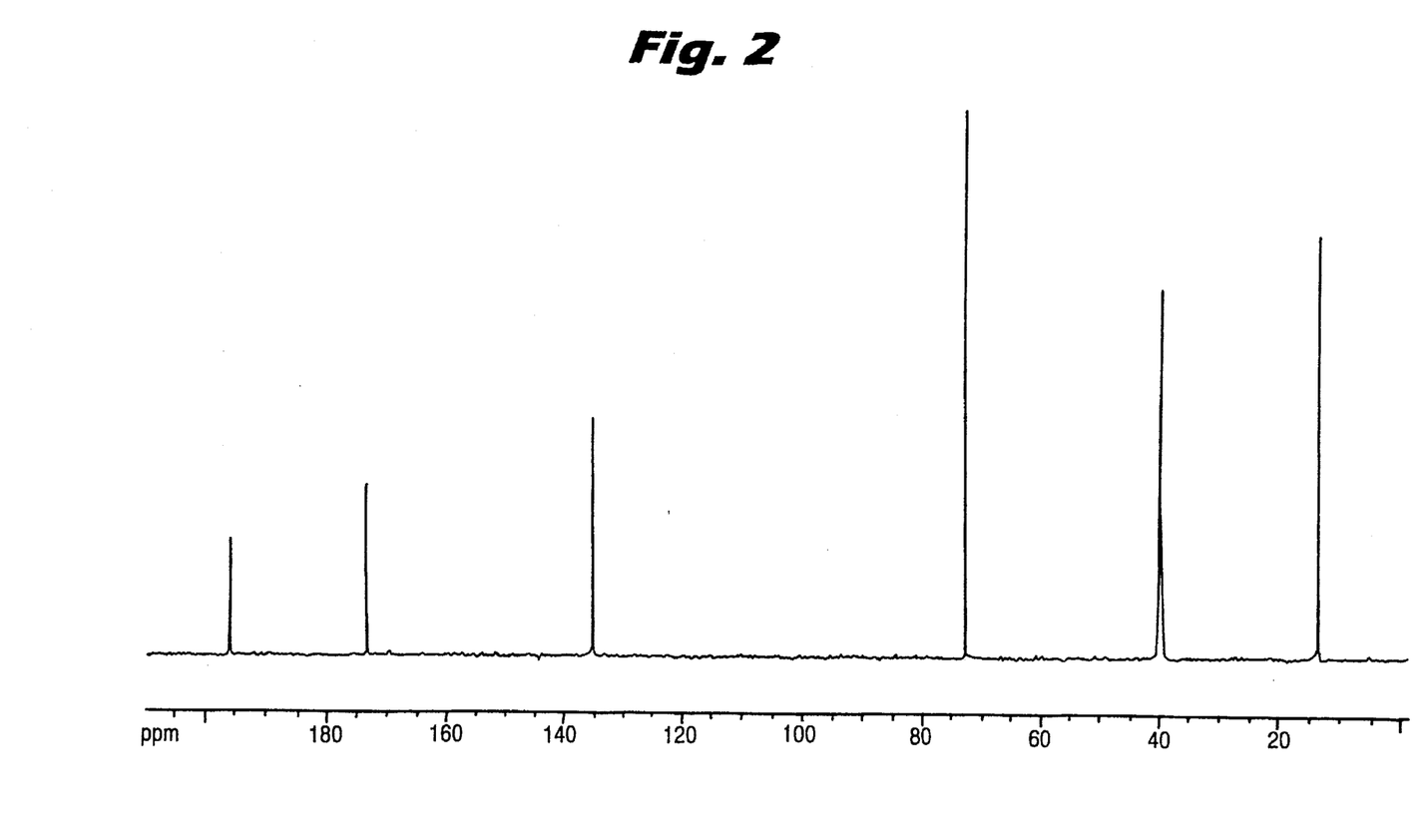
FIG. 2 is a $^{13}$C-NMR spectrum of 4-hydroxy-5-methyl-3[2H]-furanone.
Figure 3:
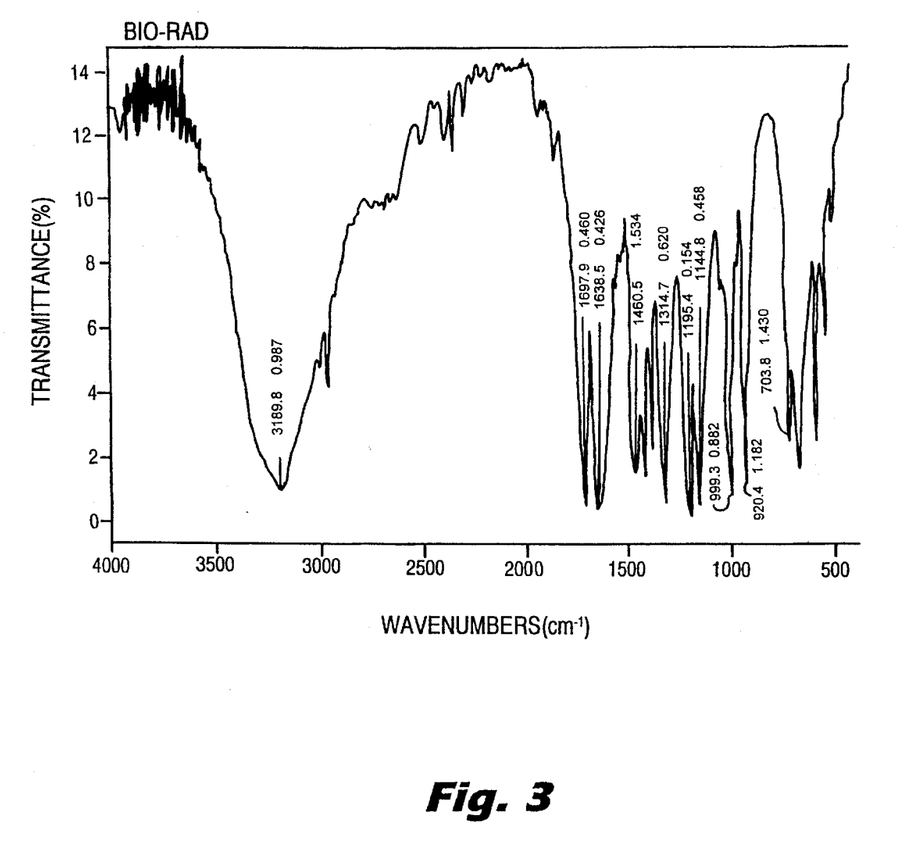
FIG. 3 is an IR spectrum of 4-hydroxy-5-methyl-3[2H]-furanone.
Figure 4:
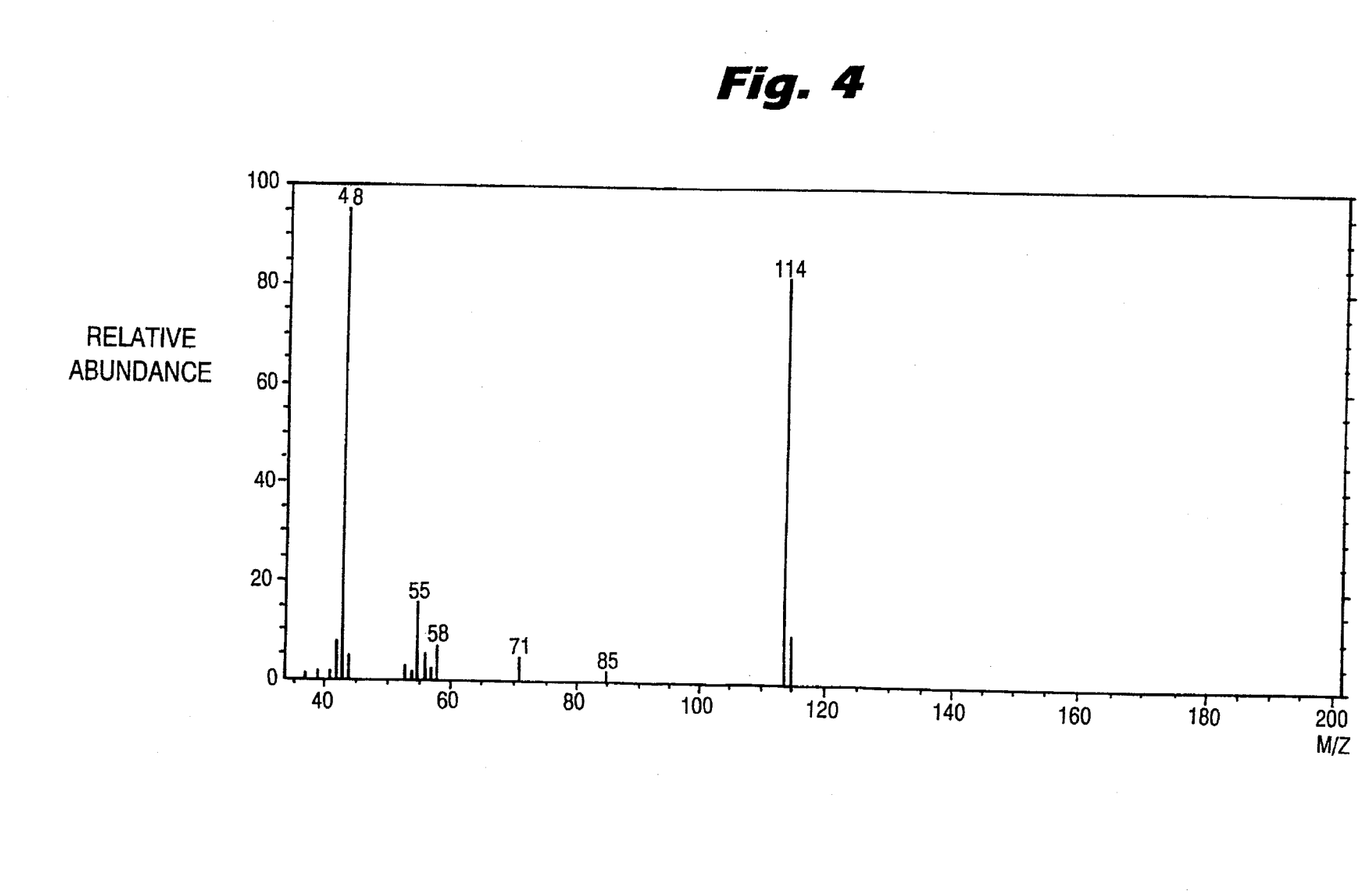
FIG. 4 is a MS spectrum of 4-hydroxy-5-methyl-3[2H]-furanone.
Figure 5:
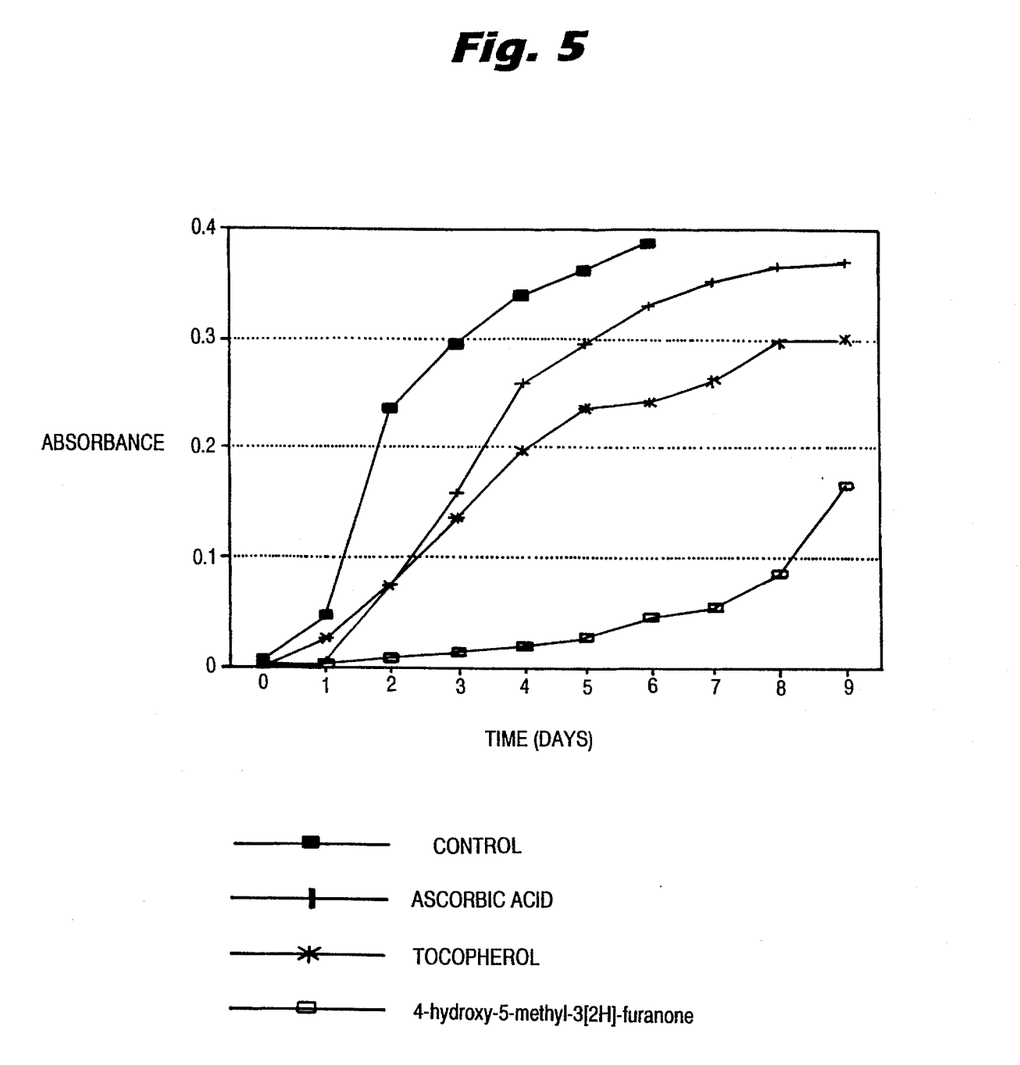
FIG. 5 is a graph showing the superior activity of preventing the oxidation of unsaturated fatty acid of 4-hydroxy-5-methyl-3[2H]-furanone.

The results are shown in FIG. 5. In FIG. 5, the longitudinal axis indicates an amount of fatty peroxide represented by an absorbance at 500 nm and the horizontal axis indicates the time in days. As can be seen from FIG. 5, 4-hydroxy-5-methyl-3[2H]-furanone can prevent more efficiently the oxidation of unsaturated fatty acid than the same amount of L-ascorbic acid or $\alpha$-tocopherol.

FORMULATIONS 1–3 AND COMPARATIVE
FORMULATIONS 1–2

Formulations containing various concentrations of 4-hydroxy-5-methyl-3[2H]-furanone were prepared by using the components shown in Table 1.

TABLE 1

| Components | Parts by weight | | | | |
| --- | --- | --- | --- | --- | --- |
| | Formulation 1 | Formulation 2 | Formulation 3 | Comp. Form. 1 | Comp. Form. 2 |
| 4-hydroxy-5-methyl-3[2H]-furanone | 0.1 | 1.0 | 3.0 | 0.03 | 5.0 |
| Beeswax | 2.0 | 2.0 | 2.0 | 2.0 | 2.0 |
| Stearic acid | 1.0 | 1.0 | 1.0 | 1.0 | 1.0 |
| Glyceryl monostearate | 1.2 | 1.2 | 1.2 | 1.2 | 1.2 |
| Liquid paraffin | 5.0 | 5.0 | 5.0 | 5.0 | 5.0 |
| Polysorbate 80 | 1.5 | 1.5 | 1.5 | 1.5 | 1.5 |
| Squalene | 5.0 | 5.0 | 5.0 | 5.0 | 5.0 |
| Cabpol | 0.1 | 0.1 | 0.1 | 0.1 | 0.1 |
| Triethanolamine | 0.2 | 0.2 | 0.2 | 0.2 | 0.2 |
| Glycerine | 10.0 | 10.0 | 10.0 | 10.0 | 10.0 |
| Perfume | q.s. | q.s. | q.s. | q.s. | q.s. |
| Preservative | q.s. | q.s. | q.s. | q.s. | q.s. |
| Pigments | q.s. | q.s. | q.s. | q.s. | q.s. |
| Distilled water | balance | balance | balance | balance | balance |
| Total | 100.0 | 100.0 | 100.0 | 100.0 | 100.0 |

COMPARATIVE FORMULATIONS 3–7

Formulations containing various concentrations of ascorbic acid or kojic acid were prepared by using the components shown in Table 2.

TABLE 2

| Components | Parts by weight | | | | |
|---|---|---|---|---|---|
| | Comp. Form. 3 | Comp. Form. 4 | Comp. Form. 5 | Comp. Form. 6 | Comp. Form. 7 |
| Ascorbic acid | 0.1 | 1.0 | 3.0 | — | — |
| Kojic acid | — | — | — | 1.0 | 3.0 |
| Beeswax | 2.0 | 2.0 | 2.0 | 2.0 | 2.0 |
| Stearic acid | 1.0 | 1.0 | 1.0 | 1.0 | 1.0 |
| Glyceryl monostearate | 1.2 | 1.2 | 1.2 | 1.2 | 1.2 |
| Liquid paraffin | 5.0 | 5.0 | 5.0 | 5.0 | 5.0 |
| Polysorbate 80 | 1.5 | 1.5 | 1.5 | 1.5 | 1.5 |
| Squalene | 5.0 | 5.0 | 5.0 | 5.0 | 5.0 |
| Cabpol | 0.1 | 0.1 | 0.1 | 0.1 | 0.1 |
| Triethanolamine | 0.2 | 0.2 | 0.2 | 0.2 | 0.2 |
| Glycerine | 10.0 | 10.0 | 10.0 | 10.0 | 10.0 |
| Perfume | q.s. | q.s. | q.s. | q.s. | q.s. |
| Preservative | q.s. | q.s. | q.s. | q.s. | q.s. |
| Pigments | q.s. | q.s. | q.s. | q.s. | q.s. |
| Distilled water | balance | balance | balance | balance | balance |
| Total | 100.0 | 100.0 | 100.0 | 100.0 | 100.0 |

EXPERIMENTAL EXAMPLE 4

Safety in the Living Body

In order to examine the safety of the formulations containing 4-hydroxy-5-methyl-3[2H]-furanone, the human body patch test was carried out using the formulations of Formulations 1 to 3 and comparative formulations 1–7.

Thus, the brachium of forty(40) healthy volunteers aging 20 to 30 years was thoroughly washed with 70% isopropyl alcohol and applied with a finn chamber containing 25 μl of each formulations. The finn chamber was closely bonded to the brachium using an adhesive tape. 24 hours later, the tape and chamber were removed, and the adherent site of the arm was wiped with a gauze to remove the remaining formulation and observed for redness(erythma), swelling and papuol. The evaluation was carried out by following scoring:

−: Negative(Score=0)

+/−: A suspicious positive(Score=0.5)

+: Weak redness(Score=1)

++: An obvious redness(Score=2)

+++: Severe redness with swelling(Score=3)

The results are shown in Table 3.

TABLE 3

| Formulations | Response(Number of subjects) | | | | | Total Score |
|---|---|---|---|---|---|---|
| | − | +/− | + | ++ | +++ | |
| Formulation 1 | 36 | 1 | 3 | | | 3.5 |
| Formulation 2 | 33 | 4 | 3 | | | 5 |
| Formulation 3 | 30 | 4 | 6 | | | 8 |
| Comp. Formul. 1 | 35 | 3 | 2 | | | 3.5 |
| Comp. Formul. 2 | 22 | 6 | 12 | | | 15 |
| Comp. Formul. 3 | 15 | 4 | 21 | | | 23 |
| Comp. Formul. 4 | 13 | 10 | 8 | 10 | 3 | 34 |
| Comp. Formul. 5 | 6 | 7 | 12 | 6 | 5 | 50.5 |
| Comp. Formul. 6 | 29 | 4 | 5 | 2 | | 11 |
| Comp. Formul. 7 | 18 | 8 | 10 | 4 | | 22 |

As can be seen from the results in Table 3, the formulations containing 4-hydroxy-5-methyl-3[2H]-furanone are less irritative than those containing ascorbic acid or kojic acid. Although, the formulations according to the invention showed weak positive responses, these are due to a very high concentration of 4-hydroxy-5-methyl-3[2H]-furanone, which is about 10 folds higher than the amount usually incorporated into common cosmetic compositions.

The formulation of Comparative Formulation 2, which contains a larger amount(5.0% by weight) of 4-hydroxy-5-methyl-3[2H]-furanone than those of Formulations 1 to 3 or Comparative Formulation 1(0.1 to 3.0% by weight), showed a certain degree of response, indicating that an appropriate amount of 4-hydroxy-5-methyl-3[2H]-furanone is between 0.1 and 3.0% by weight. The formulations containing ascorbic acid were relatively irritative to the skin when compared with others.

EXPERIMENTAL EXAMPLE 5

Tyrosinase-inhibiting Action

Tyrosinase-inhibitory effects of 4-hydroxy-5-methyl-3[2H]-furanone was compared with that of kojic acid as follows:

As an enzyme, tyrosinase purchased from SIGMA was used. Tyrosine, a substrate was dissolved into a distilled water to a concentration of 0.3 mg/ml and each 1.0 ml of the resulting solution was placed into a test tube. 1.0 ml of potassium phosphate buffer(0.1M, pH 6.8) and 0.9 ml of a serial dilutions of 4-hydroxy-5-methyl-3[2H]-furanone or kojic acid were added thereto. The resulting mixture was reacted in a 37° C. incubator for 60 minutes. Water were used to dilute the test compounds. As a control, 0.9 ml of 1:1 mixture of ethanol and water was used.

0.1 ml of tyrosinase solution (2,500 units/ml) was added and the resulting mixture was reacted in a 37° C. incubator for 10 minutes. The test tube was quickly cooled in an ice water bath to stop the reaction, and the absorbance was measured at 475 nm. The tyrosinase-inhibitory activities of the test compounds were calculated by using the following equation:

$$\text{Inhibition of tyrosinase (\%)} = 100 - \frac{\text{Absorbance of test compound}}{\text{Absorbance of control}} \times 100$$

From the inhibitions(%) of a series of dilutions of test compounds, $IC_{50}$, i.e., the concentration of test compound which inhibit tyrosinase by 50% was calculated for each test compound.

The results are shown in Table 4.

TABLE 4

| Test compound | IC$_{50}$(ppm) |
|---|---|
| 4-hydroxy-5-methyl-3[2H]-furanone | 6 |
| Kojic acid | 80 |

EXPERIMENTAL EXAMPLE 6

Inhibitive Effect of
4-hydroxy-5-methyl-3[2H]-furanone on Melanin
Formation in Melanoma Cell To a T-shaped flask containing 30 mg of Eagle's medium containing 10% fetal calf essential medium was added murine melanoma cells in an amount of 5×10$^4$ cells/30 ml. 4-hydroxy-5-methyl-3[2H]-furanone or kojic acid having a serial concentration was added to the medium and cultivation was effected at 37° C. for 48 hours. For a control, neither 4-hydroxy-5-methyl-3[2H]-furanone nor kojic acid was added. After the cultivation, the cells were collected and examined for melanin formation of the cells by observing the color of the cells.

As a result thereof, it was confirmed that 4-hydroxy-5-methyl-3[2H]-furanone can effectively inhibit the melanin formation at the concentration of 10–20 ppm while kojic acid has no effect at the concentration of 20 ppm.

EXPERIMENTAL EXAMPLE 7

Skin-whitening Action

In order to examine the action of whitening the skin of the formulations containing 4-hydroxy-5-methyl-3[2H]-furanone, the following experiment was carried out using the formulations of Formulations 1 to 3 and Comparative Formulations 1 to 7.

Thus, a certain area (2×2 cm$^2$) of both of the lower arms of forty(40) healthy volunteers was thoroughly washed with 70% isopropyl alcohol and wrapped with an aluminium foil except the area to be tested. The test area was irradiated with an UV-lay by using FL20S BLB lamp(Toshiba) and FL20S E-30 lamp(Toshiba) at a distance of 10 cm from the test area at 0.8×10$^{-7}$ erg/cm$^3$ once a day for consecutive 3 days. Then, to the irradiated area of one lower arm was applied each of test formulations three times a day for 3 weeks. The irradiated area of the other lower arm was applied no formulation. The test areas of both lower arms were compared with each other for the degree of blackening with naked eyes, and the effect of whitening the skin was evaluated: No effect, Effective, and Significant effect.

The results are shown in Table 5.

TABLE 5

| | Response(Number of subjects) | | |
|---|---|---|---|
| Formulations | No effect | Effective | Significant Effective |
| Formulation 1 | 19 | 17 | 4 |
| Formulation 2 | 6 | 12 | 22 |
| Formulation 3 | 2 | 10 | 28 |
| Comparative Formulation 1 | 34 | 6 | |
| Comparative Formulation 2 | 2 | 8 | 30 |
| Comparative Formulation 3 | 38 | 2 | |
| Comparative Formulation 4 | 38 | 2 | |
| Comparative Formulation 5 | 31 | 9 | |
| Comparative Formulation 6 | 36 | 4 | |
| Comparative Formulation 7 | 35 | 5 | |

As can be seen from the results in Table 5, the formulations containing 4-hydroxy-5-methyl-3[2H]-furanone are more effective in whitening the skin than those containing ascorbic acid or kojic acid. Particularly, the formulations of Formulations 2 and 3 and Comparative Formulation 2, which contain 4-hydroxy-5-methyl-3[2H]-furanone in an amount of from 1.0 to 5.0% by weight, were very effective in whitening the skin.

However, in consideration with the results of Experimental Example 4 showing that the formulation of Comparative Formulation which contains 5.0% of 4-hydroxy-5-methyl-3 [2H]-furanone is irritative to the skin, it is preferred to contain 0.1 to 3.0% by weight of 4-hydroxy-5-methyl-3[2H] -furanone in the light of safety and effectiveness.

FORMULATIONS 4–8

Various examples of the formulations containing the ethanolic extract or partially purified extract containing 0.5 or 9.0% by weight of 4-hydroxy-5-methyl-3[2H]-furanone, respectively are shown in Table 6.

TABLE 6

| | Parts by weight | | | | |
|---|---|---|---|---|---|
| Components | Formulation 4 | Formulation 5 | Formulation 6 | Formulation 7 | Formulation 8 |
| Ethanolic Extract in Example 5 | 20 | 30 | — | — | — |
| n-Butanol extract in Example 5 | — | — | 1.0 | 10 | 30 |
| Tween 80 | 5.0 | 5.0 | 2.0 | 5.0 | 5.0 |
| Stearic acid | 1.0 | 1.0 | 1.0 | 1.0 | 1.0 |
| Glyceryl monostearate | 1.2 | 1.2 | 1.2 | 1.2 | 1.2 |
| Polysolvate 80 | 1.5 | 1.5 | 1.5 | 1.5 | 1.5 |
| Squalene | 5.0 | 5.0 | 5.0 | 5.0 | 5.0 |
| Triethanolamine | 0.2 | 0.2 | 0.2 | 0.2 | 0.2 |
| Perfume | q.s. | q.s. | q.s. | q.s. | q.s. |
| Preservative | q.s. | q.s. | q.s. | q.s. | q.s. |
| Pigments | q.s. | q.s. | q.s. | q.s. | q.s. |
| Distilled water | balance | balance | balance | balance | balance |
| Total | 100.0 | 100.0 | 100.0 | 100.0 | 100.0 |

What is claimed is:

1. A method for producing 4-hydroxy-5-methyl-3[2H]-furanone, which comprises the steps of:
   (a) extracting 4-hydroxy-5-methyl-3[2H]-furanone from the barks or needles of the plants of *Pinaceae* species with a polar solvent;
   (b) evaporating an extract obtained in the step (a) to give a concentrate and distributing the concentrate with water and an oil-soluble solvent to give an aqueous layer;
   (c) evaporating the aqueous layer of the step (b), and subjecting the resulting concentrate to a chromatography on a reverse phase distribution column employing as an eluant a mixture of water:acetonitle:methanol= 70–95:0–20:2.5–30% by weight to give active fractions containing 4-hydroxy-5-methyl-3[2H]-furanone; and
   (d) recrystallizing the active fractions with water or methanol to give a purified 4-hydroxy-5-methyl-3[2H]-furanone.

2. The method claimed in claim 1, wherein the polar solvent employed in the step (a) is water, methanol, ethanol, propanol, or acetone, in single or mixtures thereof.

3. The method claimed in claim 1, wherein the reverse phase distribution column in the step (c) is Lichrosorb RP-18 column packed with octadecylated silica.

* * * * *